United States Patent [19]

Olive

[11] Patent Number: 5,163,920
[45] Date of Patent: Nov. 17, 1992

[54] FLOW REGULATOR DAMPER ELEMENT

[75] Inventor: Peter Olive, Needham, Mass.

[73] Assignee: Infusaid Inc., Norwood, Mass.

[21] Appl. No.: 650,371

[22] Filed: Jan. 30, 1991

[51] Int. Cl.$^5$ ............................................... A61M 5/00
[52] U.S. Cl. .................................... 604/247; 604/141; 137/504; 128/DIG. 12
[58] Field of Search .................... 604/30, 31, 133, 141, 604/186, 246, 247, 254; 128/DIG. 12; 137/499, 504

[56] References Cited

U.S. PATENT DOCUMENTS

| | | | |
|---|---|---|---|
| 163,255 | 5/1875 | Rehn | 137/504 |
| 407,656 | 7/1889 | Hawkins et al. | 137/504 |
| 2,172,865 | 9/1939 | Danel | 137/499 |
| 3,110,527 | 11/1963 | Fox | 137/504 X |
| 3,438,389 | 4/1969 | Lupin | 137/504 |
| 4,340,083 | 7/1982 | Cummins | 137/499 |

Primary Examiner—C. Fred Rosenbaum
Assistant Examiner—C. Maglione
Attorney, Agent, or Firm—Sughrue, Mion, Zinn, Macpeak & Seas

[57] ABSTRACT

A flow regulator/restrictor placed in a fluid path to passively compensate for variations in fluid pressure by deflection or movement. In one embodiment a silicon micromachined housing has a damper beam cantilevered to the interior wall between inlet and outlet. Deflections of the beam vary the volume of the restrictive gap formed between the damper beam and the interanl wall of the housing adjacent the outlet. In another embodiment the damper element is a floating element in the housing and has conformal side walls with the interior of the housing. The restrictor elements may be stacked to provide a stepped pressure drop, restrictor system.

19 Claims, 2 Drawing Sheets

FLOW REGULATOR DAMPER ELEMENT

BACKGROUND OF THE INVENTION

This invention relates to implantable medication devices and, in particular, to an implantable infusion device arranged to provide a flow of medication into the body. More particularly, this invention is directed to a component of such a device, a flow restrictor and/or regulator for purposes of providing a uniform, that is, constant flow right in the system despite varying external operating pressures.

Medication infusion devices are well known in the art such as the INFUSAID line of devices and a host patented technology as represented by U.S. Pat. Nos. 3,731,681, 4,511,355 and 4,626,244. Those three patents are representative of a host of technology which is directed to implantable devices which provide a relatively constant flow of medication from an implanted dispensing system. In these devices a flexible diaphragm or bellows defines a reservoir housing the medication. A relatively constant pressure is exerted on that diaphragm, for example, by utilizing freon or other vaporizable material to exert a pressure which is above body pressure. The medication is thus forced from the reservoir into a long capillary tube. The tube, by its length, is used as a flow limiting resistance. The medication is delivered to an infusion site at a point remote from the implantation site of the device.

In these fluid delivery systems a flow regulator may be used to provide a steady state output between the pump and the delivery site. Such devices may be accumulators, valved reservoirs and the like. There exists in the art a need to simplify such devices in implantable systems to improve reliability, reduce weight and bulk.

A standing requirement for such systems is compactness and reliability. Additionally, the materials which are used must be compatible with not only the medication which is employed, but also the in-vivo requirements.

Within the prior art various proposals have been made to decrease the size of certain components such as capillary systems utilizing silicon and micro machining concepts.

Reference is made to U.S. Pat. No. 4,537,680 which relates to an integral fluid filter and capillary wherein the capillary is formed by a groove that is etched in the surface of the silicon substrate. Silicon processing is done utilizing conventional semiconductor processing technology. A glass plate is bonded to the surface of the substrate to form a long capillary groove that has a very small cross-sectional area. Also utilizing silicon etching techniques, two comb filters are placed at each end of the capillary groove by defining a series of parallel grooves of smaller cross sectional area.

Reference is also made to U.S. Pat. No. 4,626,244 which describes an integral filter and capillary unit micromachined on a silicon substrate. The geometry of the filter and capillary unit is such that an inlet is positioned relative to a series of parallel filter grooves formed in the surface of the substrate. Medication from the inlet thus passes through the filter grooves and is collected in a series of channels of larger size. Those channels provide a supply of filtered medication to a capillary groove which is a series of reentrant loops formed on the silicon surface. The exit of the capillary channel comprises a series of parallel outlet filter grooves arranged about a central outlet collector area. The medication once passing through the outlet filter grooves to the outlet is supplied directly to the portion of the body under treatment by means of a capillary. Both the '680 and '244 patents thus define basic silicon micromachined comb and capillary systems.

Reference is made to "Normally Close Microvalve and Micropump Fabricated on a Silicon Wafer", M. Esashi et al, Proceedings of the IEEE Micro Electro Mechanical Systems, IEEE Catalog Number 89THO249-3 (1989) pp. 29-34". This article describes the fabrication of a microvalve and micropump on a silicon wafer by employing a silicon diaphragm and a piezoelectric actuator. The microvalve structure used for gas flow control comprises a valve structure mounted on a silicon substrate. An inlet is defined on the substrate with an outlet positioned by a pyrex glass cover. A piezoelectric actuator is employed to shift the silicon which has etched thereon a mesa surface which defines the valve.

While not prior art to this invention an article entitled, "Micromachined Silicon Microvalve", Ohnstein et al, IEEE Micro Electro Mechanical Systems (MEMS) 1990, IEEE Cat. No. 90 CH 2832-4 disclosed an electrostatically activated microvalve using silicon as a substrate having an orifice and a valve member made of a passivated silicon nitride. Electrodes are embedded in the structure to provide contacts for valve actuation. The valve acts as a bistable device between an open and a closed position or as a proportional flow control device as a function of applied voltage. Thus, the device operates as a valve requiring actuation for operation.

Despite such advances in the art of micromachined component structures utilizing silicon, a need still exists for components that have inhibited reducing the size of implantable devices. A reliable flow regulator-restrictor to be used with implantable systems that does not require exterior actuation and a power supply is one such requirement.

SUMMARY OF INVENTION

Given the deficiencies of the prior art, it is an object of this invention to provide for an improved silicon micromachined flow regulator.

Yet another object of this invention is to define a compact, yet reliable, flow restrictor having a minimum number of moving components.

Still another object of this invention is to define a miniaturized flow regulation device that allows for integration of electronics to measure flow rate and external conditions that account for variations therein.

These and other objects of this invention are accomplished by defining a flow restriction device comprising in a first preferred embodiment a miniaturized housing having therein a cantilever beam structure. The beam structure comprises a stem and a flow path restrictor. The stem and restrictor define a damper which is placed in the fluid flow path between an inlet and an outlet in the housing. A flow gap is defined between the damper structure and the housing to restrict flow but also provide a pressure differential between the two faces of the damper beam. The pressure difference causes deflection and thus varies the flow gap between the outlet defined in the housing and the lower surface of the damper beam.

If the pressure is fixed for the inlet and outlet, then the flow around the damper beam would be constant. If, however, inlet pressure increases and the flow around the damper tends to increase causing a pressure difference across the beam. The pressure would be greater on top of the beam closer to the inlet then on the underside. Thus, the beam would deflect toward the outlet and decrease the flow through the restrictor. Thus, compensation for higher pressure gradients occurs by restricting the flow path. The converse occurs if the inlet pressure decreases which causes the flow gap to widen.

Sensitivity of the system can be enhanced by providing flow restrictors in a series arrangement each having different damper geometries. Additionally, since the devices can be manufactured utilizing silicon micromachining capabilities, it is possible to provide integration of electronics into the devices. For example, a resistance beam can be placed on the damper beam to measure deflection. This provides an accurate measure of flow rate, and therefore, pressure drop. Similarly, a temperature sensing circuit can be placed in the device to provide an indication of temperature variations and thus, correct for variations in viscosity of the fluid passing therethrough.

In a modification of this invention the restrictor element "floats" in a housing without attachment to a wall. The position is determined by pressure differential and either magnetic or electro-static control. By providing lateral flow gaps better dimensional tolerances are obtained in the silicon etching process.

This invention will be described in greater detail by referring to the attached drawing and the description of the preferred embodiments that follow.

DESCRIPTION OF THE PREFERRED EMBODIMENTS

Figure 1:
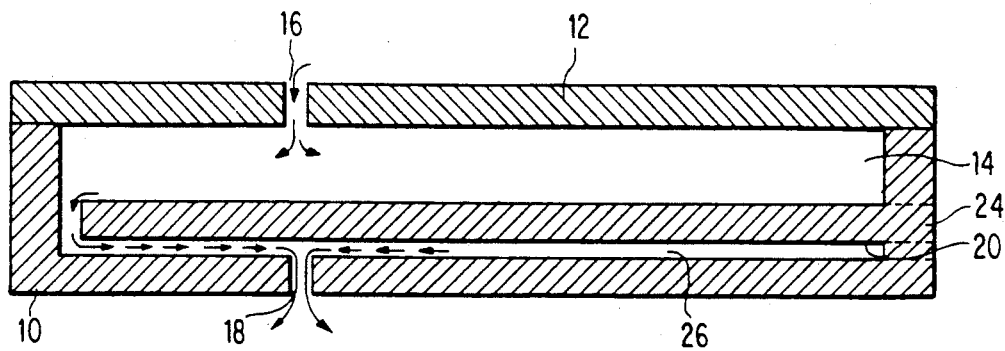
FIG. 1 is a side view of a first preferred embodiment of this invention.
Figure 2:
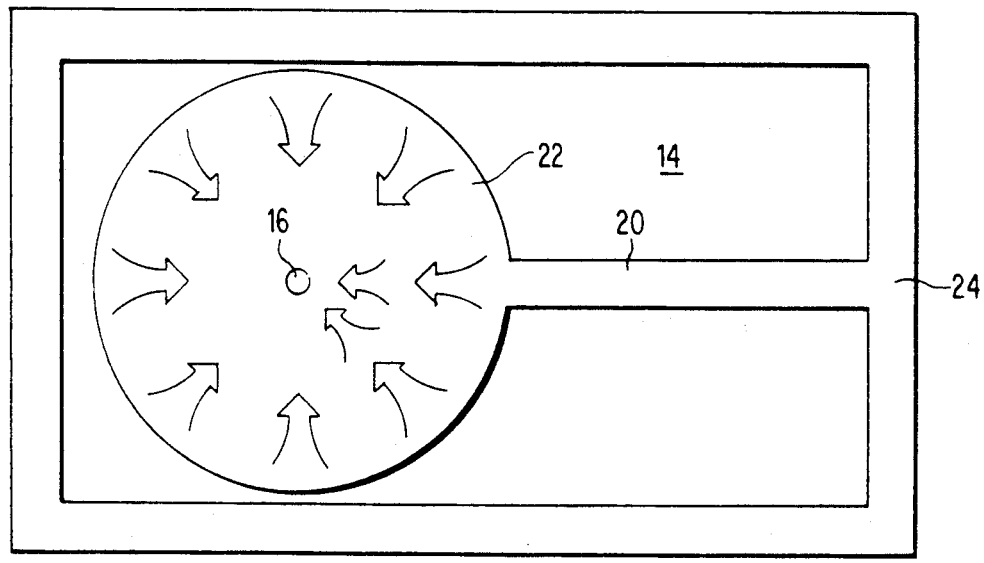
FIG. 2 is a plan view of the first embodiment of this invention.

Referring now to FIGS. 1 and 2, a first preferred embodiment of this invention is depicted In this embodiment, a housing 10 is defined by a shallow box-like structure. A top plate 12 may be either integrally formed or placed on top of the box structure 10 to define a chamber 14. The top 12 has an inlet opening 16. The housing 10 has an outlet 18 in the lower surface.

A damper beam structure is rigidly attached to the housing 16. This damper structure comprises a cantilever beam 20 and a damper plate 22. As illustrated in FIGS. 1 and 2, the beam structure is cantilevered from the wall 24 and projects within the cavity 16 to a position between the inlet 16 and the outlet 18. The damper beam structure is positioned within the cavity 14 so that it divides the volume thereof into two components of unequal volume.

The first preferred embodiment of the invention works as follows. Assuming first a fixed inlet and outlet pressure, internal pressure in the housing will be uniform and thus the flow around and under the damper beam 20 and damper plate 22 will be constant. The flow gap 26 which is established between the underside of the damper beam and the base of the housing is narrow, and thus, restricts the flow. Given the differential volume between this flow gap 26 and the remainder of the compartment 14, a pressure differential is set up across the damper plate 22. Given the cantilever construction, the plate 22 deflects to equalize the pressure as a function of volume and thus set the flow gap. That is, in order the equalize the pressure, drop across the upper and lower face of the damper plate 22, deflection of the beam occurs thereby displacing the plate relative to the restrictive gap 26 until equalization occurs by varying the volumes.

If the inlet pressure, shown by arrows at inlet 16, increases, then the flow around an under the damper plate 22 increases causing a larger pressure drop across the beam structure. This increase in pressure would cause a further deflection of the beam, downward toward the outlet 18. The volume of the gap 26 decreases thereby adding a restriction to the flow path and decreasing the flow through the restrictor. Thus, compensation for a higher inlet pressure occurs since the higher pressure gradient tends to cause an increased restriction in the flow path. The flow rate through the device then tends to be equal despite having an increase in external operating pressure.

If the pressure at the inlet 16 decreases, then the reduction in flow would tend to decrease the pressure differential across the damper plate 22. As a result the beam would deflect upward toward the inlet 16 increasing the volume of the flow gap 26. The flow path would thus become less restrictive and the flow through the outlet 18 would increase. Thus, the change in gap compensates for a change in the operating pressure which tends to make the flow rate through the device constant.

The same compensation effect would occur for changes in outlet pressures. It will be apparent that deflection of the damper plate 22 to equalize the pressure differential will provide flow regulation as a function of a change in pressure at the flow gap 26 as the outlet pressure changes.

Figure 3:
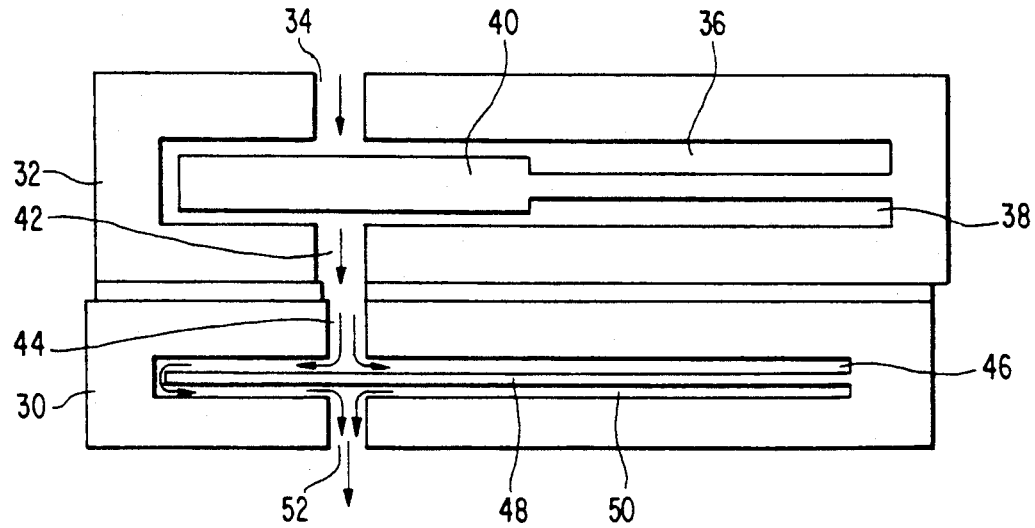
FIG. 3 is a side view of a second preferred embodiment of this invention.

Referring now to FIG. 3, a second preferred embodiment of this invention, is depicted. As is apparent from the preferred embodiment of FIG. 1 a restrictive gap must be maintained across at least one face of the damper beam. However, an increase in the total device restriction can occur by having a restrictive gap on both the top and bottom of the beam. The device, however, will become less sensitive, that is, there would be a decrease change in flow restriction compared to a device having a single gap for the same given change in pressure. To increase sensitivity the single restrictor configuration of FIGS. 1 and 2 can be stacked in a series arrangement to increase the net restriction. Such is illustrated in FIG. 3. As illustrated, this preferred embodiment comprises a pair of stacked flow regulator elements 30 and 32. An inlet to the system 34 defines a flow inlet into cavity 36. A restriction gap 38 is defined therein between the damper beam structure 40 and a first outlet 42. The damper beam 40 is cantilevered in a manner similar to that illustrated in FIGS. 1 and 2.

The stacked restrictor then comprises a second unit 30 having its inlet 44 in alignment with the outlet 42. Fluid flow, as illustrated by the arrows in 43, is thus delivered into a second chamber 46 having a second damper beam element 48. A second restriction gap 50 is defined between the damper 48 and the outlet to the system 52.

As illustrated in FIG. 3, cavity 46 has a greater internal volume than that of cavity 36. Likewise, the restrictive gap 38 has a greater volume than that of gap 50.

The size of the damper beam 40 associated with the first restrictor 32 is larger than that of beam 48 associated with the second restrictor 30.

By adjustment of these volumes and damping characteristics of the cantilever beams the restriction characteristics and thus the flow characteristics for the system can be adjusted. Moreover, by having a stacked arrangement as illustrated in FIG. 3, the restrictive gaps alternate from top to bottom, that is, they are separated by a chamber. Consequently, effects from changing the gravitational field direction are nulled by the system.

Figure 4:
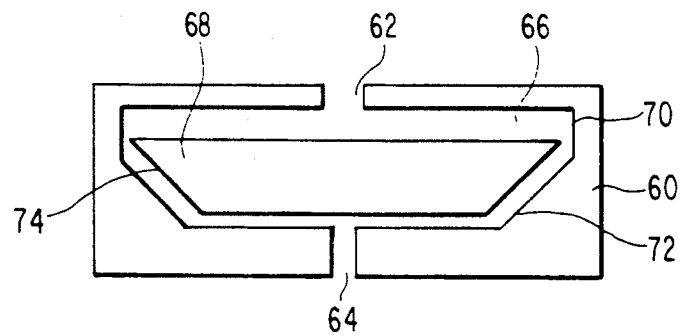
FIG. 4 is a side view of a third preferred embodiment of this invention.

Referring now to FIG. 4, a third preferred embodiment of this invention is depicted. This preferred embodiment departs from the previous two in that the flow regulator element is not coupled, that is, structurally tied to the housing. In FIG. 4, a housing, 60, made of silicon or a material capable of micromachining has an inlet 62 and an outlet 64. A cavity 66 is formed in the housing 60. Formation of the inlet 62, outlet 64 and cavity 66 can be done using conventional silicon etch techniques. While illustrated as a single unit, in cross section, it is apparent that the unit can also be made by fashioning a two place housing similar to that of FIG. 1 with a body and a top cover plate. As illustrated in FIG. 4, the cavity 66 is formed by an internal circumferential vertical side 70 and a tapered or conical side section 72. Because etch rates can be controlled and generally form tapered side walls, silicon processing allows the formation of this internal cavity diameter utilizing well established techniques.

The flow restrictor element 68 is a truncated cone having sides 74 which are conformal with the wall 72 of the cavity 66. The restrictor 68 is preferentially made of a silicon material having embedded therein conductive particles or the like. The particles which are used are a function of the type of suspension used for the flow restrictor element 68. For example, magnetic suspension can be used to position element 68 inside the cavity 66 and thus control flow rate between inlet 62 and outlet 64. If a magnetic suspension system is used then fairest particles would be embedded in the restrictor element 68. By application of an external field the positioning of the element 68 can be maintained relative to the inlet 62 and outlet 64.

An alternative technique of positioning could be by electro static suspension and/or control. Again, conventional techniques for actuation of piezoelectric elements can be employed in the context of this flow regulator device.

As is apparent from FIG. 4 the restrictor channel is defined as a function of the space which exists between the lateral walls of the restrictor element 68 and the boundary walls of the channel 66. Given the truncated conical design a more accurate micromachining by controlling the preferential etch allows for the definition of a restrictor geometry having greater precision.

As is apparent to one of working skill in this technology the devices illustrated in FIGS. 1-4 require fine geometry and close tolerances. They can be fashioned from a variety of materials. However, utilizing silicon and silicon micromachining is preferred. These processes, consistent with accepted technology in the manufacture of semiconductor devices allow for required tolerances to be maintained yet the process is economical for large scale production. The use of semiconductor processing to manufacture these flow devices is recognized in the art. For example, patterning can be done by employing silicon oxide grown on the surface of a monocrystalline silicon substrate to create an accurately position to the flow outlet. By utilizing standard photolithography and etching processes with appropriate mask patterning the device can be built using techniques which are well known in semiconductor processing.

For further reference, the disclosures in U.S. Pat. Nos. 4,537,680, 4,626,244 and an article by Angell, "Silicon Micromechanical Devices", Scientific American, April 1983, pp. 44-55" provide details. One of working skill would use semiconductor processing technology to the silicon embodiments of this invention by employing well known processing techniques.

By utilizing silicon as a material of choice for these flow restrictors additional advantages accrue. For example, electronics could be integrated onto the devices for purposes of test and monitoring. Measurement of the deflection of the damper beams can be accomplished by utilizing a resistance bridge that employs a strain gauge. Measurement of beam deflection provides a measure of flow rate and thus pressure drop across the system. Similarly, utilizing the same electronics a temperature sensing circuit can be placed on the device to provide an indication of in-vivo temperature and thus correct for changes in viscosity of the fluid which is passing through the system.

It is apparent that further changes and modifications to this invention may be made without departing from the essential scope thereof. For example, in the case of the FIG. 1 cantilever configuration a multi-point web support could be used. The restrictor would flex on the web in response to pressure deviations.

Having defined my invention, I claim:

1. A device placed in a fluid flow to equalize pressure between an inlet and an outlet comprising:
   a housing, said housing having a fluid inlet, a fluid outlet and a chamber therebetween;
   a unitary silicon damper beam in said chamber, said damper beam affixed to said housing and dividing said chamber into two regions, one of said regions defining a restrictive gap between said damper beam and said fluid outlet,
   wherein variations in pressure between said fluid inlet and said fluid outlet are compensated by deflection of said damper beam to vary the volume of said restrictive gap and thereby provide a compensated flow at said outlet.

2. The device of claim 1 wherein said damper beam comprises a cantilevered beam attached at one end to said housing and having at the opposite end a plate member positioned between said fluid inlet and said fluid outlet.

3. The device of claim 2 wherein said fluid inlet and said fluid outlet are positioned on said housing in alignment with each other and wherein said plate is symmetrical to said alignment of said fluid inlet and fluid outlet.

4. The device of claim 1 further comprising electronic means positioned on said damper beam to provide an output representative of beam deflection.

5. The device of claim 1 wherein said housing comprising a housing body and a cover member, said housing body and said damper beam comprising an integral silicon structure.

6. The device or claim 5 further comprising electronic means on said housing to determine in-vivo temperature of said device.

7. The device of claim 1 further comprising a second housing, said second housing having a fluid inlet positioned in fluid communication with said fluid outlet of said housing; said second housing having a fluid outlet and a chamber between said fluid inlet and said fluid outlet of said second chamber, a damper beam positioned in the said second housing's chamber and dividing it into two regions, one region defining a restrictive gap in said second housing between said damper beam therein and the fluid outlet of said second housing, wherein variations in pressure in said fluid flow between said inlet in said housing and said fluid outlet of said second housing are compensated by deflections of the respective damper beams.

8. A device placed in a fluid flow to equalize pressure between an inlet and an outlet comprising:

a first housing, said first housing having a fluid inlet, a fluid outlet and a chamber therebetween;

a unit damper beam in said chamber, said damper beam affixed to said housing and dividing said chamber into two regions, one of said regions defining a restrictive gap between said damper beam and said fluid outlet, wherein variations in pressure between said fluid inlet and said fluid outlet are compensated by deflection of said damper beam to vary the volume of said restrictive gap and thereby provide a compensated flow at said outlet;

a second housing, said second housing having a fluid inlet positioned in fluid communication with said fluid outlet of said first housing; said second housing having a fluid outlet and a chamber between said fluid inlet and said fluid outlet of said second housing, a damper beam positioned in the said second housing's chamber and dividing it into two regions, one region defining a restrictive gap in said second housing between said damper beam therein and the fluid outlet of said second housing, wherein variations in pressure in said fluid flow between said inlet in said housing and said fluid outlet of said second housing are compensated by deflections of the respective damper beams.

9. The device of claim 8 wherein said damper beam in said housing has a different geometry than the damper beam in said second housing.

10. The device of claim 8 wherein said chamber of said housing has a volume which is different than the volume of the chamber in said second housing.

11. An implantable medication device comprising;

a reservoir having a supply of medication, means to urge said medication out of said reservoir;

a capillary in fluid communication with said reservoir receiving said medication and delivering it to a treatment site;

a flow regulator placed between said reservoir and said capillary to passively equalize fluid pressure of medication to said capillary, said flow regulator comprising;

a housing, said housing comprising a housing body and a cover member and having an inlet in fluid communication with said reservoir, a fluid outlet in communication with said capillary and a chamber between said fluid inlet and said fluid outlet;

a damper element in said chamber, said damper element dividing said chamber into two regions, one of which defining a restrictive gap between said damper beam and said fluid outlet, said housing body and said damper element comprising an integral silicon structure wherein variations in pressure between said fluid inlet and said fluid outlet are compensated by movement of said damper element to vary the volume of said restrictive gap and thereby provide a compensated flow to said outlet.

12. The device of claim 11 wherein said damper element comprises a cantilevered beam attached to said housing at one end and having at the opposite end a plate member positioned between said fluid inlet and said fluid outlet.

13. The device of claim 12 wherein said fluid inlet and said fluid outlet are positioned on said housing in alignment with each other and wherein said plate is symmetrical to said alignment of said fluid inlet and fluid outlet.

14. The device of claim 14 further comprising electronic means on said housing to determine in-vivo temperature of said device.

15. An implantable medication device comprising;

a reservoir having a supply of medication, means to urge said medication out of said reservoir;

a capillary in fluid communication with said reservoir receiving said medication and delivering it to a treatment site;

a flow regulator placed between said reservoir and said capillary to passively equalize fluid pressure of medication to said capillary, said flow regulator comprising;

a housing, said housing having an inlet in fluid communication with said reservoir, a fluid outlet in communication with said capillary and a chamber between said fluid inlet and said fluid outlet;

a damper element in said chamber, said damper element dividing said chamber into two regions and comprising, a unitary silicon member placed in said chamber and not mounted to an internal wall.

16. The device of claim 15 further comprising electronic means positioned on said damper element to provide an output representative of element deflection.

17. An implantable medication device comprising;

a reservoir having a supply of medication, means to urge said medication out of said reservoir;

a capillary in fluid communication with said reservoir receiving said medication and delivering it to a treatment site;

a flow regulator placed between said reservoir and said capillary to passively equalize fluid pressure of medication to said capillary, said flow regulator comprising;

a housing, said housing having an inlet in fluid communication with said reservoir, a fluid outlet in communication with said capillary and a chamber between said fluid inlet and said fluid outlet;

a damper element in said chamber, said damper element dividing said chamber into two regions, one of which defining a restrictive gap between said damper beam and said fluid outlet, wherein variations in pressure between said fluid inlet and said fluid outlet are compensated by movement of said damper element to vary the volume of said restrictive gap and thereby provide a compensated flow to said outlet, a second housing, said second housing having a fluid inlet positioned in fluid communication with said fluid outlet of said housing; said second housing having a fluid outlet and a chamber between said fluid inlet and said fluid outlet of said second housing, a damper beam positioned in the said second housing's chamber and dividing it into two regions, one region defining a restrictive gap in said second housing between said damper beam therein and the fluid outlet of said second housing, wherein variations in pressure in said fluid flow between said inlet in said housing and said fluid outlet of said second housing are compensated by deflections of the respective damper beams.

18. The device of claim 17 wherein said damper element in said housing has a different geometry than the damper beam in said second housing.

19. The device of claim 17 wherein said chamber of said housing has a volume which is different than the volume of the chamber in said second housing.

* * * * *